United States Patent
Lamoureux et al.

(10) Patent No.: US 8,722,696 B2
(45) Date of Patent: May 13, 2014

(54) PROCESS FOR PREPARING PARTICLES CONTAINING AN ANTIVIRAL

(75) Inventors: Gaël Lamoureux, Le Boullay Thierry (FR); Gérard Cousin, Villemeux/Eure (FR); Daniel Joseph Christiaan Thoné, Beerse (BE)

(73) Assignee: Janssen R&D Ireland, Little Island, Co, Cork (IE)

( * ) Notice: Subject to any disclaimer, the term of this patent is extended or adjusted under 35 U.S.C. 154(b) by 871 days.

(21) Appl. No.: 12/553,545

(22) Filed: Sep. 3, 2009

(65) Prior Publication Data

US 2010/0062069 A1 Mar. 11, 2010

Related U.S. Application Data

(63) Continuation of application No. 10/564,845, filed as application No. PCT/EP2004/051545 on Jul. 19, 2004, now abandoned.

(30) Foreign Application Priority Data

Jul. 17, 2003 (FR) ........................................ 0308720
Jul. 2, 2004 (EP) ........................................ 04103156

(51) Int. Cl.
*A61K 9/14* (2006.01)
*A61K 31/505* (2006.01)
*A61K 9/16* (2006.01)

(52) U.S. Cl.
CPC ............. *A61K 31/505* (2013.01); *A61K 9/1676* (2013.01)
USPC ........................................ 514/275; 424/489

(58) Field of Classification Search
CPC ............................ A61K 31/505; A61K 9/1676
USPC ........................................... 514/275; 424/489
See application file for complete search history.

(56) References Cited

U.S. PATENT DOCUMENTS

| | | | | |
|---|---|---|---|---|
| 4,016,254 A | * | 4/1977 | Seager | ............ 424/497 |
| 5,776,495 A | | 7/1998 | Duclos et al. | |
| 6,027,747 A | | 2/2000 | Terracol et al. | |
| 2001/0007678 A1 | * | 7/2001 | Baert et al. | ............ 424/464 |

FOREIGN PATENT DOCUMENTS

| | | |
|---|---|---|
| EP | 1103252 | 5/2001 |
| WO | WO 97/04749 | 2/1997 |
| WO | WO 99/50250 | 10/1999 |
| WO | WO 99/50256 | 10/1999 |
| WO | WO 00/27825 | 5/2000 |
| WO | WO 01/22938 | 4/2001 |
| WO | WO 03/16306 | 2/2003 |

OTHER PUBLICATIONS

Vasconcelos, T., et al. "Solid Dispersions as Strategy to Improve Oral Bioavailability of Poor Water Soluble Drugs", Drug Discovery Today, vol. 12, No. 23/24 (2007) pp. 1068-1075.
International Search Report mailed Jan. 24, 2005 for related International Application No. PCT/EP2004/051545.

* cited by examiner

*Primary Examiner* — Bong-Sook Baek
(74) *Attorney, Agent, or Firm* — Michael J. Atkins

(57) ABSTRACT

A process for preparing a particle comprising a co-precipitate surrounding a neutral hydrophilic carrier, said process comprising spraying an organic solution on a neutral hydrophilic carrier, said solution comprising at least one triazine or pyrimidine active ingredient having HIV inhibiting properties, one surface active agent, and one hydrophilic polymer, wherein the spraying of whole of the solution occurs in at least two separate steps, each of these steps followed by a grinding step of the product obtained at the end of the preceding step.

5 Claims, No Drawings

PROCESS FOR PREPARING PARTICLES CONTAINING AN ANTIVIRAL

CROSS REFERENCE TO RELATED APPLICATIONS

This application is a continuation of pending U.S. application Ser. No. 10/564,845, filed Jan. 13, 2006, now abandoned which in turn is a national stage of PCT Application No. PCT/EP2004/051545, filed Jul. 19, 2004, which claims priority for French Application No. 0308720, filed Jul. 17, 2003 and EPO Patent Application No. 04103156.8, filed Jul. 2, 2004, all of which are hereby incorporated by reference in their entirety.

This invention concerns a process for preparing particles containing antiviral pyrimidines and triazines in the form of a co-precipitate, particles prepared by this process, and pharmaceutical dosage forms comprising these particles.

An increasing number of active ingredients having interesting pharmacological activities are hard to formulate into standard oral formulations. This because increased structural complexity or the presence of lipophilic moieties results in a very limited solubility in aqueous media and concomitant reduced or even in some cases absent absorption of the active ingredient in the gastro-intestinal tract. This typically translates into an impaired or a very low bioavailability so that high doses of the active need to be administered to patients in order to achieve effective concentration levels. Therefore a single dose administration may be insufficient for the drug to be effective requiring a multi-dose administration either at once or by a multiple daily dosing, or both.

Since long, formulations have been developed aimed at overcoming these problems. Among these, solid dispersions of active ingredients have been found to be particularly attractive in that they often provide considerable improvement in the solubility and concomitant bioavailability of the active ingredients formulated in this manner. Solid dispersions in general consist of an active ingredient that is dispersed in a hydrophilic medium, usually a polymer.

Solid dispersions are usually obtained using two methods. On the one hand they can be obtained via evaporation of a solution consisting of the active ingredient and an inert polymeric material, and on the other via co-fusion of the aforementioned components, with subsequent solidification. In the former instance, the resulting product is referred to as co-precipitate, in the latter as co-melt. Depending on the preparation technique used, co-precipitates can be a solid mass, but they can also be made in particulate form. Solid dispersions in particulate form have become attractive formulation forms for active ingredients with problematic bioavailabilty.

Solid dispersions in particulate form face a number of challenges. First of all they should allow the highest possible level of dissolution and release of the active ingredient in order to ensure sufficient and effective bioavailability thereof.

Secondly, the particles preferably should have a narrow particle size distribution and be of a size that is appropriate for the preparation of dosage forms for oral administration, while containing sufficient high levels of the active ingredient.

Thirdly, the particles should be sufficiently stable over time and able to withstand unfavorable temperature and humidity conditions, such as those commonly used in stability studies, for example storage for extended periods of time at 30° C./60% RH (Relative Humidity), or at 40° C./75% RH.

In certain cases, a solid dispersion in itself is not sufficient to guarantee a sufficient level of bioavailability and of effectiveness of the active ingredient that needs to be administered. To that purpose a number of improvements have been proposed such as the addition of certain ingredients. International patent application WO 97/04749 concerns a preparation process for solid dispersions wherein the active ingredient(s) is/are dissolved in an organic solvent otherwise containing a highly hydrophilic cyclic amide, and advantageously a surface active agent, with the resulting organic solution subsequently evaporated dry, then milled and sieved. The cyclic amide is a polyvinylpyrrolidone with a molecular weight that varies between 10,000 and 50,000.

Certain classes of pyrimidines and triazines have been disclosed in WO-99/50250, WO-99/50256, WO-00/27825 and WO-03/016306 as potent HIV-inhibiting agents. Many of these compounds, in particular those lacking solubilizing groups such as carboxyl or amino groups, have low to very low solubility and need to be formulated in specially adapted formulations in order to provide sufficient bioavailabilty. Providing formulations for oral dosage forms that deliver an effective amount of these active ingredients poses a particular challenge. This is even more critical given the fact that these active ingredients are HIV-inhibiting agents where it is an absolute requirement that blood plasma levels surpass a certain threshold, which marks the level under which the active no longer is effective amount so that the virus is adequately suppressed thereby avoiding mutations.

WO-01/22938 is concerned with pharmaceutical compositions of pyrimidine and triazine antiviral compounds, in particular the pyrimidines and triazines mentioned above, comprising particles obtainable by melt-extruding a mixture comprising one or more antiviral compounds and one or more appropriate water-soluble polymers and subsequently milling said melt-extruded mixture. A disadvantage associated with melt-extrusion is that the components need to be heated to obtain a homogenous melt so that the active ingredient may be subject to degradation.

The pyrimidine and triazine antivirals mentioned above need to be administered in unit doses containing relatively high amounts of active ingredient, for example amounts which are in the range of 100 mg to 800 mg per unit dose requiring relatively high amounts of solid dispersion forming polymer. Solid dispersions in particle form containing these active ingredients pose a particular challenge in that a lot of material has to be sprayed on an inert core of restricted size. Indeed, the size of the core is limited because otherwise too much of the core material is present in the end formulation giving rise to unpractically large dosage forms. Moreover particles on which a lot of material has been spayed on tend to agglomerate and therefore are much more difficult to further process.

The present invention is aimed at overcoming these problems in that it provides processes for preparing formulations comprising particles wherein a co-precipitate is applied as a layer surrounding a neutral hydrophilic core and wherein the co-precipitate comprises, at least one HIV-inhibitory pyrimidine or triazine, one surface-active agent, and one hydrophilic polymer. These particles show improved bioavailability of active ingredients even when almost insoluble in aqueous media, and increase both the dissolution rate and the amount of active ingredient that is released in vitro and in vivo.

The layer surrounding the neutral hydrophilic carrier is a solid dispersion comprising a co-precipitate, which is soluble in water or in physiological media, such as for example in gastric juice.

The particles prepared according to the process of this invention have the additional advantage of improving the problem of particle agglomeration that is frequently faced when spraying large quantities of coating solutions, by grinding the particles not only after finalization of the spraying step, but also during this step.

The size reduction resulting from grinding thus allows to continue spraying on particles of smaller size, that are less likely to agglomerate than particles obtained in a single spraying step with a continuous increase of particle size.

Thus in one aspect, the present invention concerns a process for preparing a particle comprising a co-precipitate surrounding a neutral hydrophilic carrier, said process comprising spraying an organic solution on a neutral hydrophilic carrier, said solution comprising at least one triazine or pyrimidine active ingredient having HIV inhibiting properties, one surface active agent, and one hydrophilic polymer, wherein the spraying of whole of the solution occurs in at least two separate steps, each of these steps followed by a grinding step of the product obtained at the end of the preceding step.

In a particular aspect, the present invention concerns the preparation of particles comprising a co-precipitate surrounding a neutral hydrophilic carrier comprising the following steps:
 a) preparing a solution comprising at least one triazine or pyrimidine active ingredient having HIV inhibiting properties, a hydrophilic polymer, and a surface active agent, in an organic solvent;
 b) spraying part of the solution obtained in step a) on a neutral hydrophilic carrier;
 c) grinding of the particles obtained in step b);
 d) spraying of the remaining quantity of organic solution on the particles obtained in step c) carrier, and
 e) final grinding of the particles obtained in step d).

The spraying/grinding sequence (steps b to d) may be done once, or repeated several times, depending on the volume of the solution intended for spraying and the growth kinetics of the particle during the course of the spraying step.

The carrier used in the process of the invention preferably takes the form of neutral hydrophilic particles, which function as a core on which the solution as specified herein containing the pyrimidine or triazine active ingredient, is sprayed.

All of the organic solution may be prepared in a single step. However, in order to avoid excess evaporation of the organic solvents, it is preferable to prepare each fraction of the solution just prior to the spraying step.

Spraying of the organic solution may be carried out in a conventional fluidized bed drier equipped with a spraying device using the top or bottom spraying process. In a preferred embodiment of the process of the invention, all the spraying steps are carried out in a fluidized bed, equipped with an anti-deflagration device.

In certain embodiments, in particular in case of larger batches, the material obtained after grinding (as in step c)), may de partitioned in two or more parts, preferably of equal size. Each part may then be sprayed separately (as in step d)) and ground, whereupon all the resulting material is blended. In alternative embodiments, each of the parts, after spaying (as in step d)) may be ground with a different grinder. The selection of these variants can be done to optimize particle size and particle size distribution.

The fluidized bed is equipped with a spraying nozzle, the position and orientation of which may be selected such that it enables control over the kinetics of the growth of the particles and avoids problems of sticking, linked to the type of active ingredient, to the qualitative and quantitative composition of the sprayed coating solution, and to various parameters of the procedure (e.g. temperature, air pressure, and the rate of spraying).

The particles are dried after spraying of the organic solution. Drying may be carried out on trays, or directly inside the equipment used in the spraying step or in a tumble drier. Drying may be carried out either just after spraying of the organic solution, or immediately following the grinding of particles.

Grinding may be carried out using any type of equipment designed for this particular purpose, and may include use of an oscillating or a blade type grinder. Examples are the FITZMILL rotation type grinder, or the FREWITT oscillating type grinder that are equipped with rotors that force particles through a grid with calibrated openings. The FORPLEX is stator rotor grinder type equipped with pins to which particles are projected at a certain feed rate. The type of grinder and the grinding parameters, e.g. speed of grinding, will define the final particle size and particle size distribution.

Different grinders may be used after each spraying step. Moreover, grinding may be done partially on one type of grinder and finished on another type of grinder. All these variants are selected to determine the size and size distribution of the product after grinding.

The process of the invention is particularly useful for active ingredients that are almost insoluble in water, that is for active ingredients where one part is soluble in 1000 parts of water, or more than 1000 parts of water, more in particular for active ingredients that are practically insoluble in water, that is for active ingredients of which one part is soluble in 10,000 parts of water, or more than 10,000 parts of water.

The triazine or pyrimidine active ingredient having HIV inhibiting properties for use in the process of the present invention and in the products obtained therewith preferably is a triazine or pyrimidine derivative that has low solubility in water or aqueous media. Low solubility in this context refers to a compound having a solubility of less than 2 mg/ml or less than 1 mg/ml, or even lower, e.g. less than 0.5 mg/ml or 0.2 mg/ml or even 0.1 mg/ml. Low solubility of active ingredients moreover is meant to include active ingredients that are substantially insoluble, e.g. having a solubility below 0.05 mg/ml or even 0.01 mg/ml. Solubilities are in water or in usual aqueous media that are physiologically relevant (e.g. having a pH between 1-8). However, triazines or pyrimidines of higher solubility may be used as well, e.g. having solubilities up to 5 mg/ml or 10 mg/ml or even 20 mg/ml The triazine or pyrimidine active ingredients for use in the processes and resulting products of this invention in particular are those lacking ionizable groups, e.g. carboxyl or amine groups.

Of interest are triazine or pyrimidine active ingredients disclosed in any of WO99/50250, WO99/50256, WO00/27825 or WO03/016306, either specifically or falling under any of the definitions specified in these patent applications, which applications are incorporated herein by reference.

The triazine or pyrimidine active ingredient having HIV inhibiting properties for use in the processes and products of this invention in particular is:
 (a) an antiviral compound of formula $$(I\text{-}A)$$

a N-oxide, a pharmaceutically acceptable addition salt or a stereochemically isomeric form thereof, wherein
Y is $CR^5$ or N;
A is CH, $CR^4$ or N;
n is 0, 1, 2, 3 or 4;

Q is —NR¹R² or when Y is CR⁵ then Q may also be hydrogen;

R¹ and R² are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or R¹ and R² taken together may form pyrrolidinyl, piperidinyl, morpholinyl, azido or mono- or di($C_{1-12}$alkyl)amino$C_{1-4}$alkylidene;

R³ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and each R⁴ independently is hydroxy, halo, $C_{1-6}$alkyl, $C_{1-6}$alkyloxy, cyano, amino carbonyl, nitro, amino, trihalomethyl, trihalomethyloxy, or when Y is CR⁵ then R⁴ may also represent $C_{1-6}$alkyl substituted with cyano or aminocarbonyl;

R⁵ is hydrogen or $C_{1-4}$alkyl;

L is —X¹—R⁶ or —X²-Alk-R⁷ wherein
R⁶ and R⁷ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl; or when Y is CR⁵ then R⁶ and R⁷ may also be selected from phenyl substituted with one, two, three, four or five substituents each independently selected from aminocarbonyl, trihalomethyloxy and trihalomethyl; or when Y is N then R⁶ and R⁷ may also be selected from indanyl or indolyl, each of said indanyl or indolyl may be substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl; when R⁶ is optionally substituted indanyl or indolyl, it is preferably attached to the remainder of the molecule via the fused phenyl ring. For instance, R⁶ is suitably 4-, 5-, 6- or 7-indolyl;
X¹ and X² are each independently —NR³—, —NH—NH—, —N=N—, —O—, —S—, —S(=O)— or —S(=O)₂—;
Alk is $C_{1-4}$alkanediyl; or
when Y is CR⁵ then L may also be selected from $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl;

aryl is phenyl or phenyl substituted with one, two, three, four or five substituents each independently selected from halo, $C_{1-6}$alkyl, $C_{1-6}$alkyloxy, cyano, nitro and trifluoromethyl;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy; or (b) an antiviral compound of formula

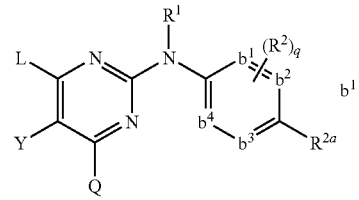

an N-oxide, a pharmaceutically acceptable addition salt, or a stereochemically isomeric forms thereof, wherein
-b¹=b²-C(R²ᵃ)=b³-b⁴= represents a bivalent radical of formula

| | |
|---|---|
| —CH=CH—C(R²ᵃ)=CH—CH= | (b-1); |
| —N=CH—C(R²ᵃ)=CH—CH= | (b-2); |
| —CH=N—C(R²ᵃ)=CH—CH= | (b-3); |
| —N=CH—C(R²ᵃ)=N—CH= | (b-4); |
| —N=CH—C(R²ᵃ)=CH—N= | (b-5); |
| —CH=N—C(R²ᵃ)=N—CH= | (b-6); |
| —N=N—C(R²ᵃ)=CH—CH= | (b-7); | q is 0, 1, 2; or where possible q is 3 or 4;

R¹ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl;

R²ᵃ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;

each R² independently is hydroxy, halo, $C_{1-6}$alkyl optionally substituted with cyano or —C(=O)R⁶, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)ₚR⁶, —NH—S(=O)ₚR⁶, —C(=O)R⁶, —NHC(=O)H, —C(=O)NHNH₂, —NHC(=O)R⁶, —C(=NH)R⁶ or a radical of formula

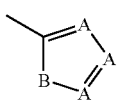

(c)

wherein each A independently is N, CH or CR⁶;
B is NH, O, S or NR⁶;
p is 1 or 2; and R⁶ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from
$C_{3-7}$cycloalkyl,
indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or L is —X—$R^3$ wherein
$R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$; and
X is —$NR^1$—, —NH—NH—, —N=N—, —O—, —C(=O)—, —CHOH—, —S—, —S(=O)— or —S(=O)₂—;

Q represents hydrogen, $C_{1-6}$alkyl, halo, polyhalo$C_{1-6}$alkyl or —$NR^4R^5$; and $R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$R⁶, —NH—S(=O)$_p$R⁶, —C(=O)R⁶, —NHC(=O)H, —C(=O)NHNH₂, —NHC(=O)R⁶, —C(=NH)R⁶, aryl and Het; or $R^4$ and $R^5$ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)R⁶, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R⁶, —NH—S(=O)$_p$R⁶, —C(=O)R⁶, —NHC(=O)H, —C(=O)NHNH₂, —NHC(=O)R⁶, —C(=NH)R⁶ or aryl;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy; Het is meant to include all the possible isomeric forms of the heterocycles mentioned in the definition of Het, for instance, pyrrolyl also includes 2H-pyrrolyl; the Het radical may be attached to the remainder of the molecule of formula (I-B) through any ring carbon or heteroatom as appropriate, thus, for example, when the heterocycle is pyridinyl, it may be 2-pyridinyl, 3-pyridinyl or 4-pyridinyl. or (c) a compound of formula

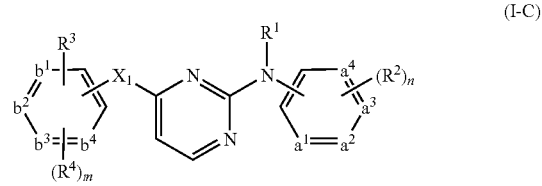

(I-C)

a N-oxide, a pharmaceutically acceptable addition salt or a stereochemically isomeric form thereof, wherein
-$a^1$=$a^2$-$a^3$=$a^4$- represents a bivalent radical of formula —CH=CH—CH=CH— (a-1);

—N=CH—CH=CH— (a-2);

—N=CH—N=CH— (a-3);

—N=CH—CH=N— (a-4);

—N=N—CH=CH— (a-5);

-$b^1$=$b^2$-$b^3$=$b^4$- represents a bivalent radical of formula

—CH=CH—CH=CH— (b-1);

—N=CH—CH=CH— (b-2);

—N=CH—N=CH— (b-3);

—N=CH—CH=N— (b-4);

—N=N—CH=CH— (b-5);

n is 0, 1, 2, 3 or 4; and in case -$a^1$=$a^2$-$a^3$=$a^4$- is (a-1), then n may also be 5;

m is 1, 2, 3 and in case -$b^1$=$b^2$-$b^3$=$b^4$- is (b-1), then m may also be 4;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

each $R^2$ independently is hydroxy, halo, $C_{1-6}$alkyl optionally substituted with cyano or —C(=O)R⁶, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(=O)$_p$R⁶, —NH—S(=O)$_p$R⁶, —C(=O)R⁶, —NHC(=O)H, —C(=O)NHNH₂, —NHC(=O)R⁶, —C(=NH)R⁶ or a radical of formula

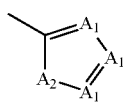

(c)

wherein each $A_1$ independently is N, CH or $CR^6$; and $A_2$ is NH, O, S or $NR^6$;

$X_1$ is $-NR^5-$, $-NH-NH-$, $-N=N-$, $-O-$, $-C(=O)-$, $C_{1-4}$alkanediyl, $-CHOH-$, $-S-$, $-S(=O)_p-$, $-X_2-C_{1-4}$alkanediyl- or $-C_{1-4}$alkanediyl-$X_2-$;

$X_2$ is $-NR^5-$, $-NH-NH-$, $-N=N-$, $-O-$, $-C(=O)-$, $-CHOH-$, $-S-$, $-S(=O)_p-$;

$R^3$ is $NHR^{13}$; $NR^{13}R^{14}$; $-C(=O)-NHR^{13}$; $-C(=O)-NR^{13}R^{14}$; $-C(=O)-R^{15}$; $-CH=N-NH-C(=O)-R^{16}$; $C_{1-6}$alkyl substituted with one or more substituents each independently selected from cyano, $NR^9R^{10}$, $-C(=O)-NR^9R^{10}$, $-C(=O)-C_{1-6}$alkyl or $R^7$; $C_{1-6}$alkyl substituted with one or more substituents each independently selected from cyano, $NR^9R^{10}$, $-C(=O)-NR^9R^{10}$, $-C(=O)-C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, $-C(=O)-NR^9R^{10}$, $-C(=O)-C_{1-6}$alkyl or $R^7$; $C_{1-6}$alkyloxy$C_{1-6}$alkyl optionally substituted with one or more substituents each independently selected from cyano, $NR^9R^{10}$, $-C(=O)-NR^9R^{10}$, $-C(=O)-C_{1-6}$alkyl or $R^7$; $C_{2-6}$alkenyl substituted with one or more substituents each independently selected from halo, cyano, $NR^9R^{10}$, $-C(=O)-NR^9R^{10}$, $-C(=O)-C_{1-6}$alkyl or $R^7$; $C_{2-6}$alkynyl substituted with one or more substituents each independently selected from halo, cyano, $NR^9R^{10}$, $-C(=O)-NR^9R^{10}$, $-C(=O)-C_{1-6}$alkyl or $R^7$; $-C(=N-O-R^8)-C_{1-4}$alkyl; $R^7$ or $-X_3-R^7$;

$X_3$ is $-NR^5-$, $-NH-NH-$, $-N=N-$, $-O-$, $-C(=O)-$, $-S-$, $-S(=O)_p-$, $-X_2-C_{1-4}$alkanediyl-, $-C_{1-4}$alkanediyl-$X_{2a}$-, $-C_{1-4}$alkanediyl-$X_{2b}$-$C_{1-4}$alkanediyl, $-C(=N-OR^8)-C_{1-4}$alkanediyl-;

with $X_{2a}$ being $-NH-NH-$, $-N=N-$, $-O-$, $-C(=O)-$, $-S-$, $-S(=O)_p-$; and with $X_{2b}$ being $-NH-NH-$, $-N=N-$, $-C(=O)-$, $-S-$, $-S(=O)_p-$;

$R^4$ is halo, hydroxy, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, $C_{1-6}$alkyloxycarbonyl, $C_{1-6}$alkylcarbonyl, formyl, amino, mono- or di($C_{1-6}$alkyl)amino or $R^7$;

$R^5$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl or $C_{1-6}$alkylcarbonyloxy; $C_{1-6}$alkyloxy$C_{1-6}$alkylcarbonyl substituted with $C_{1-6}$alkyloxycarbonyl;

$R^6$ is $C_{1-4}$alkyl, amino, mono- or di($C_{1-4}$alkyl)amino or polyhalo$C_{1-4}$alkyl;

$R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkyl, carbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $-CH(=N-O-R^8)$, $R^{7a}$, $-X_3-R^{7a}$ or $R^{7a}-C_{1-4}$alkyl;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $-CH(=N-O-R^8)$;

$R^8$ is hydrogen, $C_{1-4}$alkyl, aryl or aryl$C_{1-4}$alkyl;

$R^9$ and $R^{10}$ each independently are hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; $-CH(=NR^{11})$ or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$, $R^7$; or $R^9$ and $R^{10}$ may be taken together to form a bivalent or trivalent radical of formula

 $-CH_2-CH_2-CH_2-CH_2-$ (d-1)

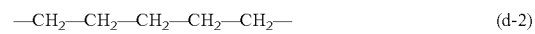 $-CH_2-CH_2-CH_2-CH_2-CH_2-$ (d-2)

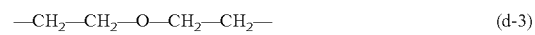 $-CH_2-CH_2-O-CH_2-CH_2-$ (d-3)

 $-CH_2-CH_2-S-CH_2-CH_2-$ (d-4)

 $-CH_2-CH_2-NR^{12}-CH_2-CH_2-$ (d-5)

 $-CH_2-CH=CH-CH_2-$ (d-6)

 $=CH-CH=CH-CH=CH-$ (d-7)

$R^{11}$ is cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ is hydrogen or $C_{1-4}$alkyl;

$R^{13}$ and $R^{14}$ each independently are $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ is $C_{1-6}$alkyl substituted with cyano or aminocarbonyl;

$R^{16}$ is $C_{1-6}$alkyl optionally substituted with cyano or aminocarbonyl, or $R^7$;

p is 1 or 2;

aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$ alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro polyhalo$C_{1-6}$alkyl, polyhalo$C_{1-6}$alkyloxy, aminocarbonyl, $R^2$ or —$X_3$—$R^7$.

As used in the foregoing definitions and hereinafter halo defines fluoro, chloro, bromo and iodo; polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoro-ethyl and the like; in case more than one halogen atoms are attached to an alkyl group within the definition of polyhalomethyl or polyhalo$C_{1-6}$alkyl, they may be the same or different; $C_{1-4}$alkyl as a group or part of a group encompasses the straight and branched chained saturated hydrocarbon radicals having from 1 to 4 carbon atoms such as, for example, methyl, ethyl, propyl, butyl and the like; $C_{1-6}$alkyl as a group or part of a group encompasses the straight and branched chained saturated hydrocarbon radicals as defined in $C_{1-4}$alkyl as well as the higher homologues thereof containing 5 or 6 carbon atoms such as, for example pentyl or hexyl; $C_{1-6}$alkyl as a group or part of a group group encompasses the straight and branched chained saturated hydrocarbon radicals as defined in $C_{1-6}$alkyl as well as the higher homologues thereof containing 7 to 10 carbon atoms such as, for example, heptyl, octyl, nonyl or decyl; $C_{1-12}$alkyl as a group or part of a group encompasses the straight and branched chained saturated hydrocarbon radicals as defined in $C_{1-10}$alkyl as well as the higher homologues thereof containing 11 or 12 carbon atoms such as, for example, undecyl, dodecyl and the like; $C_{1-4}$alkylidene as a group or part of a group defines bivalent straight and branched chained hydrocarbons having from 1 to 4 carbon atoms such as, for example, methylene, ethylidene, propylidene, butylidene and the like; $C_{1-4}$alkanediyl as a group or part of a group encompasses those radicals defined under $C_{1-4}$alkylidene as well as other bivalent straight and branched chained hydrocarbons having from 1 to 4 carbon atoms such as, for example, 1,2-ethanediyl, 1,3-propanediyl, 1,4-butanediyl and the like; $C_{3-7}$cycloalkyl as a group or part of a group is generic to cyclopropyl, cyclobutyl, cyclopentyl, cyclohexyl and cycloheptyl; $C_{3-10}$alkenyl as a group or part of a group defines straight and branch chained hydrocarbon radicals containing one double bond and having from 3 to 10 carbon atoms such as, for example, 2-propenyl, 2-butenyl, 2-pentenyl, 3-pentenyl, 3-methyl-2-butenyl, 3-hexenyl, 3-heptenyl, 2-octenyl, 2-nonenyl, 2-decenyl and the like, whereby the carbon atom attached to the pyrimidine ring is preferably an aliphatic carbon atom; $C_{3-10}$alkynyl as a group or part of a group defines straight and branch chained hydrocarbon radicals containing one triple bond and having from 3 to10 carbon atoms such as, for example, 2-propynyl, 2-butynyl, 2-pentynyl, 3-pentynyl, 3-methyl-2-butynyl, 3-hexynyl, 3-heptynyl, 2-octynyl, 2-nonynyl, 2-decynyl and the like, whereby the carbon atom attached to the pyrimidine ring is preferably an aliphatic carbon atom; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-10}$alkenyl defines straight and branched chain hydrocarbon radicals having from 2 to 10 carbon atoms containing a double bond such as the groups defined for $C_{2-6}$alkenyl and heptenyl, octenyl, nonenyl, decenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; $C_{2-10}$alkynyl defines straight and branched chain hydrocarbon radicals having from 2 to 10 carbon atoms containing a triple bond such as the groups defined for $C_{2-6}$alkynyl and heptynyl, octynyl, nonynyl, decynyl and the like; $C_{1-3}$alkyl as a group or part of a group encompasses the straight and branched chain saturated hydrocarbon radicals having from 1 to 3 carbon atoms such as, methyl, ethyl and propyl; $C_{4-10}$alkyl encompasses the straight and branched chain saturated hydrocarbon radicals as defined above, having from 4 to 10 carbon atoms. The term $C_{1-6}$alkyloxy defines straight or branched chain saturated hydrocarbon radicals such as methoxy, ethoxy, propyloxy, butyloxy, pentyloxy, hexyloxy, 1-methylethyloxy, 2-methylpropyloxy, 2-methylbutyloxy and the like; $C_{3-6}$cycloalkyloxy is generic to cyclopropyloxy, cyclobutyloxy, cyclopentyloxy and cyclohexyloxy.

As used herein before, the term (═O) forms a carbonyl moiety when attached to a carbon atom, a sulfoxide group when attached once to a sulfur atom, and a sulfonyl group when attached twice to a sulfur atom.

When any variable (e.g. aryl, $R^3$, $R^4$ in formula (I-A) etc.) occurs more than one time in any constituent, each definition is independent.

Lines drawn into ring systems from substituents indicate that the bond may be attached to any of the suitable ring atoms. For instance for compounds of formula (I-A), $R^4$ can be attached to any available carbon atom of the phenyl or pyridyl ring.

The addition salts as mentioned herein are meant to comprise the therapeutically active addition salt forms which the compounds of formula (I-A), (I-B) or (I-C) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of the present invention are able to form. Said salts can conveniently be obtained by treating the compounds of the present invention containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salts also comprises the hydrates and the solvent addition forms which the compounds of formula (I-A), (I-B) or (I-C) are able to form. Examples of such forms are e.g. hydrates, alcoholates and the like.

Interesting compounds of formula (I-A) are those wherein Y is $CR^5$ or N; A is CH, $CR^4$ or N; n is 0, 1, 2, 3 or 4; Q is —$NR^1R^2$; $R^1$ and $R^2$ are each independently selected from hydrogen, hydroxy, $C_{1-12}$alkyl, $C_{1-12}$alkyloxy, $C_{1-12}$ alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, aminocarbonyl, aminocarbonylamino, mono- or di(C$_{1-6}$alkyl)amino, aryl and Het; or R$^1$ and R$^2$ taken together may form pyrrolidinyl, piperidinyl, morpholinyl, azido or mono- or di(C$_{1-12}$alkyl)aminoC$_{1-4}$alkylidene; R$^3$ is hydrogen, aryl, C$_{1-6}$alkylcarbonyl, C$_{1-6}$alkyl, C$_{1-6}$alkyloxycarbonyl, C$_{1-6}$alkyl substituted with C$_{1-6}$alkyloxycarbonyl; each R$^4$ independently is hydroxy, halo, C$_{1-6}$alkyl, C$_{1-6}$alkyloxy, cyano, aminocarbonyl, nitro, amino, trihalomethyl, trihalomethyloxy; R$^5$ is hydrogen or C$_{1-4}$alkyl; L is C$_{1-4}$alkyl; L is —X$^1$—R$^6$ or —X$^2$-Alk-R$^7$ wherein R$^6$ and R$^7$ each independently are phenyl or phenyl substituted with one, two, three, four or five substituents each independently selected from halo, hydroxy, C$_{1-6}$alkyl, C$_{1-6}$alkyloxy, C$_{1-6}$alkylcarbonyl, C$_{1-6}$alkyloxycarbonyl, formyl, cyano, nitro, amino, and trifluoromethyl, X$^1$ and X$^2$ are each independently —NR$^3$—, —NH—NH—, —N=N—, —O—, —S—, —S(=O)— or —S(=O)$_2$—, and Alk is C$_{1-4}$alkanediyl; aryl is phenyl or phenyl substituted with one, two, three, four or five substituents each independently selected from halo, C$_{1-6}$alkyl, C$_{1-6}$alkyloxy, cyano, nitro and trifluoromethyl; Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy.

Preferred compounds of formula (I-A) are
4-[[4-amino-6-[(2,6-dichlorophenyl)methyl]-2-pyrimidinyl]amino]benzonitrile;
4-[[4-[(2,4,6-trimethylphenyl)amino]-2-pyrimidinyl]amino]benzonitrile;
4-[[4-[(2,6-dimethylphenyl)amino]-2-pyrimidinyl]amino]benzonitrile;
4-[[4-(2,4,6-trimethylphenoxy)-2-pyrimidinyl]amino]benzonitrile;
4-[[4-[(2,6-dichlorophenyl)thio]-2-pyrimidinyl]amino]benzonitrile;
4-[[4-[(2,4-dichloro-6-methylphenyl)amino]-2-pyrimidinyl]amino]benzonitrile;
4-[[2-[(cyanophenyl)amino]-4-pyrimidinyl]amino]-3,5-dimethylbenzonitrile;
4-[[4-[(2,4-dibromo-6-fluorophenyl)amino]-2-pyrimidinyl]amino]benzonitrile;
4-[[4-[(2,4,6-trichlorophenyl)amino]-2-pyrimidinyl]amino]benzonitrile;
4-[[4-[(2,4,6-trimethylphenyl)amino]-2-pyrimidinyl]amino]benzonitrile;
4-[[2-amino-6-[(2,4,6-trimethylphenyl)amino]-4-pyrimidinyl]amino]benzonitrile;
4-[[2-[(4-cyanophenyl)amino]-5-methyl-4-pyrimidinyl]amino-3,5-dimethylbenzonitrile;
[[2-[(4-cyanophenyl)amino]-5-methyl-4-pyrimidinyl]amino]-3,5-dimethylbenzonitrile;
4-[[4-amino-6-[(2,4,6-trimethylphenyl)amino]-1,3,5-triazin-2-yl]amino]benzonitrile;
4-[[4-(hydroxyamino)-6-[(2,4,6-trimethylphenyl)amino]-1,3,5-triazin-2-yl]amino]-benzonitrile;
4-[[4-(hydroxyamino)-6-[(2,4,6-trichlorophenyl)amino]-1,3,5-triazin-2-yl]amino]-benzonitrile;
4-[[4-(4-acetyl-2,6-dimethylphenoxy)-6-amino-1,3,5-triazin-2-yl]amino]benzonitrile;
[[4-[(5-acetyl-2,3-dihydro-7-methyl-1H-inden-4-yl)oxy]-6-amino-1,3,5-triazin-2-yl]-amino]benzonitrile;
4-[[4-amino-6-[(2-chloro-4,6-dimethylphenyl)amino]-1,3,5-triazin-2-yl]amino]-benzonitrile;
4-[[4-amino-6-[(2,6-dibromo-4-methylphenyl)amino]-1,3,5-triazin-2-yl]amino]-benzonitrile; the N-oxides, the pharmaceutically acceptable addition salts and the stereochemically isomeric forms thereof.

Most preferred is 4-[[4-[(2,4,6-trimethylphenyl)amino]-2-pyrimidinyl]amino]benzonitrile, or a pharmaceutically acceptable salt thereof, also referred to as TMC120, which can be represented by the following chemical structure:

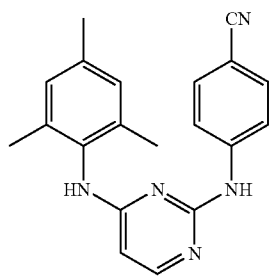 [SMILES: Cc1cc(C)c(Nc2ccnc(Nc3ccc(C#N)cc3)n2)c(C)c1]

Interesting compounds of formula (I-B) are those wherein one or more of the following restrictions apply:
i) -b$^1$=b$^2$-C(R$^{2a}$)=b$^3$-b$^4$= is a radical of formula (b-1);
ii) q is 0;
iii) R$^{2a}$ is cyano or —C(=O)NH$_2$, preferably R$^{2a}$ is cyano;
iv) Y is cyano, —C(=O)NH$_2$ or a halogen, preferably a halogen;
v) Q is hydrogen or —NR$^4$R$^5$ wherein R$^4$ and R$^5$ are preferably hydrogen;
vi) L is —X—R$^3$ wherein X is preferably NR$^1$, O or S, most preferably X is NH, and R$^3$ is substituted phenyl with C$_{1-6}$alkyl, halogen and cyano as preferred substituents.

Another interesting group of compounds of formula (I-B) are those compounds of formula (I-B) wherein L is —X—R$^3$ wherein R$^3$ is 2,4,6-trisubstituted phenyl, each substituent independently selected from chloro, bromo, fluoro, cyano or C$_{1-4}$alkyl.

Also interesting are those compounds of formula (I-B) wherein Y is chloro or bromo and Q is hydrogen or amino.

Particular compounds of formula (I-B) are those compounds of formula (I-B) wherein the moiety in the 2 position of the pyrimidine ring is a 4-cyano-anilino group.

Further particular compounds of formula (I-B) are those compounds of formula (I-B) wherein the moiety in the 2 position of the pyrimidine ring is a 4-cyano-anilino group, L is —X—R$^3$ wherein R$^3$ is a 2,4,6-trisubstituted phenyl, Y is a halogen and Q is hydrogen or NH$_2$.

Most preferred compounds of formula (I-B) are:
4-[[4-amino-5-chloro-6-[(2,4,6-trimethylphenyl)amino]-2-pyrimidinyl]amino]-benzonitrile;
4-[[5-chloro-4-[(2,4,6-trimethylphenyl)amino]-2-pyrimidinyl]amino]benzonitrile;
4-[[5-bromo-4-(4-cyano-2,6-dimethylphenoxy)-2-pyrimidinyl]amino]benzonitrile;
4-[[4-amino-5-chloro-6-[(4-cyano-2,6-dimethylphenyl)amino]-2-pyrimidinyl]amino]-benzonitrile;
4-[[5-bromo-6-[(4-cyano-2,6-dimethylphenyl)amino]-2-pyrimidinyl]amino]-benzonitrile;
4-[[4-amino-5-chloro-6-(4-cyano-2,6-dimethylphenyloxy)-2-pyrimidinyl]amino]-benzonitrile; and 4-[[4-amino-5-bromo-6-(4-cyano-2,6-dimethylphenyloxy)-2-pyrimidinyl]amino]-benzonitrile; the N-oxides, the pharmaceutically acceptable addition salts, quaternary amines and the stereochemically isomeric forms thereof.

The most preferred compound of formula (I-B) is 4-[[4-amino-5-bromo-6-(4-cyano-2,6-dimethylphenyloxy)-2-pyrimidinyl]amino]-benzonitrile; or a pharmaceutically acceptable addition salt thereof, which usually is designated as TMC125 and which can be represented by formula:

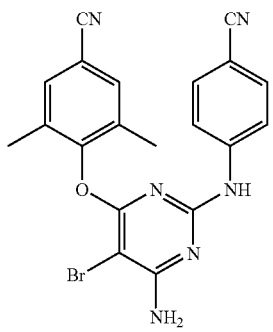 [SMILES: Cc1cc(C#N)cc(C)c1Oc1nc(Nc2ccc(C#N)cc2)nc(N)c1Br]

Particular compounds of formula (I-C) are those having the formula

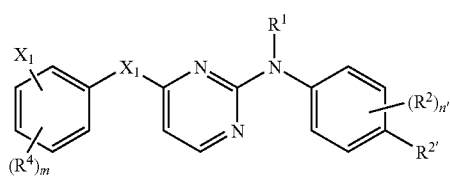

(I-C-1)

wherein
$R^1$, $R^2$, $R^3$, $R^4$ and $X_1$ are as defined above;
n is 0, 1, 2 or 3;
$R^{2'}$ is halo, $C_{1-6}$alkyl, trihalomethyl, trihalomethyloxy, cyano, aminocarbonyl, $C_{1-6}$alkyl substituted with cyano or aminocarbonyl;
and $R^{2'}$ is positioned in the para position in respect of the $NR^1$ moiety.

Further particular compounds of formula (I-C) are those having the formula (I-C-1) wherein $R^{2'}$ is cyano, aminocarbonyl or $C_{1-6}$alkyl substituted with cyano or aminocarbonyl.

Further particular compounds are those compounds of formula (I-C) or (I-C-1) wherein one or more, preferably all of the following restrictions apply:
a) n is at least 1, in particular 1; or n' is 0;
b) $R^2$ or $R^{2'}$ is cyano;
c) m is 1, 2 or 3;
d) $R^4$ is $C_{1-6}$alkyl, especially methyl; nitro; amino; halo; $C_{1-6}$alkyloxy or $R^7$;
e) $R^3$ is $R^7$, $NR^{13}R^{14}$, —C(=O)$R^{15}$, —CH=N—NH—C(=O)$R^{16}$, —C(=O)NHR$^{13}$, —C(=O)NR$^{13}$R$^{14}$, C(=N—OR$^8$)—C$_{1-4}$alkyl, C$_{1-6}$alkyl substituted with cyano, C$_{1-6}$alkyl substituted twice with cyano, C$_{1-6}$alkyl substituted with NR$^9$R$^{10}$, C$_{1-6}$alkyl substituted with hydroxy and cyano, C$_{1-6}$alkyl substituted with hydroxy and $R^7$, C$_{1-6}$alkyloxy C$_{1-6}$alkyl, C$_{1-6}$alkyloxy C$_{1-6}$alkyl substituted with cyano, C$_{2-6}$alkenyl substituted with $R^7$, C$_{2-6}$alkenyl substituted with cyano, C$_{2-6}$alkenyl substituted twice with cyano, C$_{2-6}$alkenyl substituted with cyano and $R^7$, C$_{2-6}$alkenyl substituted with cyano and —C(=O)—C$_{1-6}$alkyl, C$_{2-6}$alkenyl substituted with cyano and halo, C$_{2-6}$alkenyl substituted with —C(=O)—NR$^9$R$^{10}$, C$_{2-6}$alkenyl substituted with halo, C$_{2-6}$alkenyl substituted twice with halo or C$_{2-6}$alkenyl substituted with NR$^9$R$^{10}$;
f) $X_3$ is —C(=O)—, —CH$_2$—C(=O)—, or —C(=N—OR$^8$)—C$_{1-4}$alkanediyl-;
g) $X_1$ is NH or O;
h) $R^1$ is hydrogen or $C_{1-4}$alkyl.

Preferred compounds of formula (I-C) are:

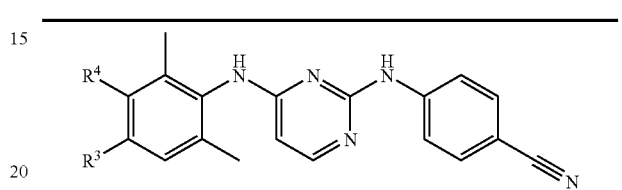

| Comp No. | $R^3$ | $R^4$ |
|---|---|---|
| 1 | —CH=CH—CN | H |
| 2 | —C(CH$_3$)=CH—CN | H |
| 3 | —CH=C(CH$_3$)—CN | H |

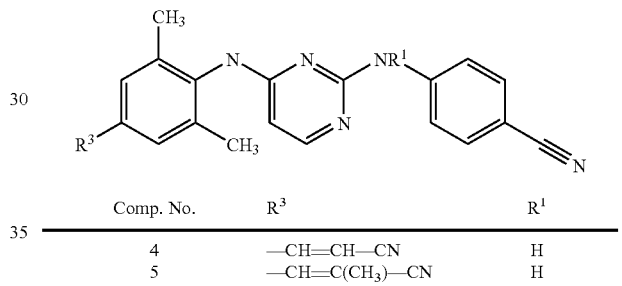

| Comp. No. | $R^3$ | $R^1$ |
|---|---|---|
| 4 | —CH=CH—CN | H |
| 5 | —CH=C(CH$_3$)—CN | H |

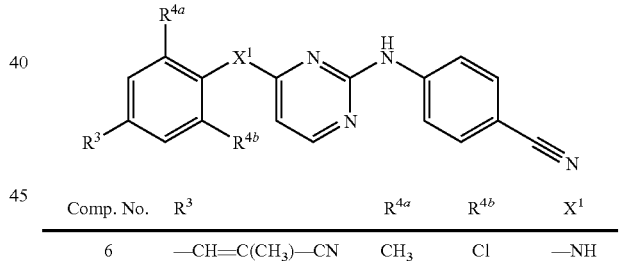

| Comp. No. | $R^3$ | $R^{4a}$ | $R^{4b}$ | $X^1$ |
|---|---|---|---|---|
| 6 | —CH=C(CH$_3$)—CN | CH$_3$ | Cl | —NH |
| 7 | —CH=CH—CN | CH$_3$ | 2-furanyl | —NH |
| 8 | —CH=C(CH$_3$)—CN | CH$_3$ | Br | —NH |
| 9 | —CH=CH—CN | CH$_3$ | Br | —NH |
| 10 | —CH=CH—CN | CH$_3$ | Cl | —NH |

Of particular interest is compound 1 listed above, or a pharmaceutically acceptable salt thereof, which compound is also referred to as TMC278.

The active ingredient may be present in the particle in an amount that may vary from 1 to 60% by weight, in particular from 5 to 50% by weight, more in particular from 10 to 40% or from 10 to 30% by weight.

The inert hydrophilic carrier may consist of any chemically and pharmaceutically inert excipient, existing in particle form, crystalline or amorphous, for example sugars or sugar derivatives such as lactose, preferably Extra Fine Lactose (EFK), sucrose, hydrolyzed starch (maltodextrins), celluloses, or mixtures thereof such as sucrose and starch; or mixtures with a cellulose base may also be used for the preparation of the inert carrier.

The inert hydrophilic carrier is present in an amount that may be as high as 95% by weight, in particular from 1-95% by weight, more in particular from 5-50% by weight, further in particular from 10 to 40% or from 10-30% by weight.

The unit particle size of the inert hydrophilic carrier may range from 50 µm to 500 µm, preferably from 90 µm to 200 µm. Preferred is a carrier that is spherically shaped.

Suitable hydrophilic polymers are polyvinylpyrrolidones, cellulose derivatives, acrylic polymers or polyethylene glycols. Of particular interest is polyvinylpyrrolidone, in particular the latter polymer having a molecular weight ranging from 10,000 to 50,000.

Appropriate cellulose derivatives comprise hydroxyalkylated celluloses, for example, hydroxypropylmethylcellulose, hydroxypropylcellulose, hydroxymethylcellulose, hydroxypropylmethylcellulose phthalate and hydroxypropylmethylcellulose acetosuccinate.

Preferred is hydroxypropylmethylcellulose (HPMC), more in particular the latter polymer having an apparent viscosity ranging from 2.4 to 18 cP, and even more preferably ranging from 2.4 to 5 cP.

The acrylic polymer may be selected among ammonium methacrylate copolymer, polyacrylate, polymethacrylate, and methacrylic acid copolymer.

The polyethylene glycol may be chosen among polymers with a molecular weight ranging from 1,000 to 20,000.

The weight ratio of the hydrophilic polymer to the active ingredient ranges preferably from 10:1 to 1:2.

The surface-active agent may be selected among cationic, anionic, non-ionic or amphoteric surfactants, separately, or as a mixture.

The surface-active agent may be selected among compounds such as sodium laurylsulfate; the monooleate, monolaurate, monopalmitate, monostearate, trioleate, tristearate, or any other polyoxyethylenated sorbitan fatty ester, preferably Tween® 20, 40, 60 or 80; ethoxylated fatty acid glycerides, said fatty acids being saturated or not, and containing at least 8 carbon atoms; poloxamers such as poloxamer 188; bloc copolymers of ethylene oxide/propylene oxide such as Pluronic® F68 or F87; stearyl alcohol, cetostearyl alcohol; lecithin; cholesterol; polyethoxylated castor oil; polyethoxylated fatty alcohol ethers, such as Brij®; and polyethoxylated stearates.

The surface-active agent is advantageously present in amounts that may vary between 0.1 and 20% by weight, in particular between 1-10% by weight, more in particular between 1-5% by weight, compared to the total resulting mass.

The organic solvent may be selected among an alcohol such as ethanol, isopropanol; an ether such as tetrahydrofuran, isopropyl ether; a ketone such as acetone, methylethylketone; methylene chloride; or any mixture thereof.

The amount of solvent used should is selected such that it takes into account the solubility of the various components of the organic solution.

In a further aspect the present invention also concerns a particle comprising, or in an alternative aspect, consisting of, a co-precipitate applied in a layer surrounding a neutral hydrophilic carrier and comprising at least one antiviral pyrimidine or triazine, at least one surface-active agent, and at least one hydrophilic polymer. The neutral hydrophilic carrier preferably is present as a core.

In still a further aspect the present invention also concerns a particle containing or in an alternative aspect, consisting of a co-precipitate applied in a layer surrounding a neutral hydrophilic carrier and comprising at least one antiviral pyrimidine or triazine, at least one surface-active agent, and at least one hydrophilic polymer, obtainable or obtained by the process described herein.

The size of particles usually ranges from 50 µm to 1000 µm, preferably from 100 µm to 800 µm, more preferably from 150 µm to 300 µm, e.g. about 250 µm, and is determined using conventional methods, for example with a set of sieves containing calibrated openings, or using laser diffraction.

In a preferred embodiment of the invention, the particles of the invention contain:
  from 15 to 40% in weight of an inert hydrophilic carrier, preferably lactose, more preferably lactose EFK;
  from 15 to 30% in weight of an active ingredient as defined herein, which active ingredient preferably is TMC120, TMC125, or TMC278.
  from 30 to 60% in weight of a hydrophilic polymer, preferably HPMC;
  from 1 to 10% in weight of a surface-active agent, preferably a non-ionic surfactant such as polysorbate, in particular selected from the group comprising polysorbates 20 to 80.

The particles according to the invention may be used directly, or in a mixture, with excipients typically used in the pharmaceutical art for the preparation of a pharmaceutical form intended for oral administration, such as for example, a capsule, or a tablet, chemically compatible with the active ingredient(s).

Thus in still a further aspect, this invention provides a pharmaceutical composition comprising particles as specified herein and one or more further excipients. The invention also provides an oral dosage form comprising particles as specified herein, or comprising a pharmaceutical composition comprising particles as specified herein.

Examples of excipients comprise diluents, disintegrating agents, bulking agents, lubricants, antistatic agents, binders or any other adjuvants used in preparing pharmaceutical formulations.

The diluent may be selected among sugars such as sucrose, lactose, fructose, dextrose, or polyols with less than 13 atoms of the carbon, such as mannitol, xylitol, sorbitol, maltitol, lactitol, erythritol, dicalcium phosphate, tricalcium phosphate, or microcrystalline cellulose, separately or in combination.

The diluent is used in an amount ranging from 20 to 90% in weight, preferably from 30 to 60% in weight, calculated based on the weight of the tablet.

The diluent is preferably used in a directly compressible form, with an average particle diameter ranging from 100 µm to 500 µm, or in the form of a powder with an average particle size that is less than 100 µm, said powder being used separately, or in a mixture with the directly compressible product.

The disintegrating agent is selected from the group comprising in particular cross-linked sodium carboxymethylcellulose designated by the term croscarmellose, cross-linked polyvinyl pyrrolidones designated by the term crospovidone, and mixtures thereof.

The disintegrating agent is used in an amount ranging from 1 to 20% in weight, preferably from 5 to 15% in weight, calculated based on the weight of the tablet.

The bulking agent is selected from the group comprising microcrystalline cellulose, starches, modified starches, such as carboxymethyl starch or sodium glycolated starch, alginic acid, or sodium alginate, and mixtures thereof.

The bulking agent is used in an amount ranging from 1 to 15% in weight, calculated on the basis of the tablet weight.

The lubricant is selected from the group comprising magnesium stearate, stearic acid, sodium stearyl fumarate, polyoxyethylene glycols, sodium benzoate, a pharmaceutically acceptable oil, preferably dimethicone, paraffin oil, or cotton seed oils, and mixtures thereof.

The lubricant is used in an amount of up to 2%, preferably from 0.02 to 2% in weight, more preferably from 0.5 to 1% in weight, calculated based on the weight of the tablet.

According to a first variant of preparing the dosage forms of this invention, the total amount of lubricant is incorporated in the mixture of excipients to be compressed; in a second variant, at least a fraction of the lubricant is sprayed on the walls of the matrix and the punches at the moment of compression; the lubricant is then in the form of a powder, for example magnesium stearate or a liquid, for example liquid paraffin oil.

The quantities of lubricant used during the internal and/or external steps are carefully adjusted so as to avoid excess that would interfere with cohesion of the powder bed during compression.

The antistatic agent may be selected from the group comprising micronized or non-micronized talc, colloidal silica (e.g. Aerosil®200), processed silica (e.g. Aerosil®R972), or precipitated silica (e.g. Syloid®FP244), and mixtures thereof.

The antistatic agent is used in an amount of up to 5% in weight, calculated based on the weight of the tablet.

The binder is used in dry form, and may consist of starch, sugar, polyvinylpyrrolidone, or carboxymethylcellulose, separately or as a mixture.

The binder is used in an amount of up to 15% in weight, preferably less that 10% in weight, calculated based on the weight of the tablet.

Adjuvants may also be added to the mixture formulated for capsules, or for compression, and may be selected from pH adjusting agents, systems allowing to produce effervescence, in particular carbon dioxide generators of the type used as pH adjusters, or surface active agents.

The invention also concerns pharmaceutical dosage forms comprising the particles as described herein.

Preparation of pharmaceutical dosage forms comprising the invention particles may consist of the following steps:
  dry mixing of the particles obtained according to the procedures previously described, with the excipients;
  compression of the mixture or transfer of the mixture to capsules to obtain a unit form.

In order to avoid sticking, the punches and/or the internal walls of the compression matrix (the dies) may be treated with a suitable lubricant such as any of the lubricants mentioned above.

According to one embodiment, the preparation of the dosage forms comprises first mixing the active ingredient and all of the other excipients, including the lubricant whereupon the mixture is compressed. In another embodiment, only part of the lubricant is added, the remainder being sprayed on the punches and/or dies. In still another embodiment, the preparation of the dosage forms comprises two steps, first mixing the active ingredient with all of the compression excipients except for the internal lubricant, and then in a second step, the lubricant is added completely or in part to the mixture. When added in part to the mixture, the remaining part of the lubricant is sprayed on the punches and/or the dies.

According to still another embodiment of the invention all of the lubricant is sprayed on the punches and/or the dies, and the step of adding lubricant to the mixture is then obviously omitted.

Compression of the mixture may be carried out with any compressing apparatus used in the art, e.g. by a rotational compression machine.

The hardness of the tablet is adapted so that the resulting brittleness, as measured by European Pharmacopoeia methods, is less than 2% by weight, preferably 1% by weight.

The shape of the tablets may be round, oval, oblong, with a surface that is flat, concave or convex, and optionally may be embossed. In general, the tablets have a mass that ranges from 0.1 to 2.0 grams, and a diameter size ranging from 6 to 18 mm. In case of oblong tablets, the length may vary between 10 and 30 mm, e.g. about 21 mm and the width between 5 and 15 mm e g about 10 mm Preferably the length of the oblong tablets is about double the size of the width. The size and weight of the tablets will be determined by the amount of active ingredient that is incorporated therein.

EXAMPLES

Example 1

1. Preparation of the Particles
Production was carried out on a GPCG1 fluidized bed in Bottom Spray mode.

The spraying solution was prepared by dissolving TMC125 in a mixture of solvents 96% alcohol/methylene with HPMC 2910 ScPs (supplied by Dow Chemical) and polysorbate 20 (Montanox®20, supplied by SEPPIC).

Lactose EFK (supplied by HMS) was introduced on the fluidized bed and the solution was sprayed in the bottom spray mode. The granules were dried on a fluidized bed and milled using a FITZMILL grinder with a 790-μm grid.

After the spraying step, the resulting granules were dried on the fluidized bed.

Preparation of the Spraying Solution
Composition of the Spraying Solutions

| Raw materials | Quantity (kg) |
| --- | --- |
| TMC125 | 11.67 |
| HPMC 2910 5 cPs | 35.00 |
| Montanox 20DF | 1.17 |
| Methylene chloride | 860.00 |
| Ethyl alcohol 96% | 83.33 |
| Total | 991.17 |

Six batches of the spraying solutions (hereafter referred to as solutions 1 to 6) were made according to the following operating method:
1. Pour the alcohol and methylene chloride in the tank after weighing them in the same container
2. Put under stirring, add TMC125 and wait until complete dissolution
3. Dissolve Montanox 20 DF under stirring
4. Dissolve HPMC 2910 cPs under stirring until it is completely dissolved
1. 5. Readjust the solution weight by adding methylene chloride to make up for the evaporation which occurred during the solution preparation.

Solutions 1 & 2 were prepared at first. Then, solutions 3 & 4 and solutions 5 & 6 were prepared respectively during the spraying of solutions 1 & 2 and solutions 3 & 4.

Layering with Solution 1 and 2
1. 63 kg of Lactose EFK were introduced into the fluidized bed GPCG 120 and solutions 1 and 2 were sprayed. The granulates were then dried in the fluidized bed GPCG 120 for approximately fifteen minutes.

2. The granulates were sieved on a 1.60 mm screen after this first layering step. The undersized granulates were milled half part on a Fitzmill grinder equipped with a 790 μm screen and half part on a Forplex grinder to optimize the process time.
3. The oversized granulates were milled on a Fitzmill grinder equipped with a 790 μm screen.
4. The resulting mass of granulates was then divided into two equivalent parts: Part A and Part B. Each part was composed of half of granulates milled with a Forplex grinder and half of granulates milled with a Fitzmill grinder to have an homogeneous particle size distribution.

Layering with Solutions 3 and 4

These two solutions were sprayed on part A. The resulting granulates were dried in the fluidized bed GPCG 120 for approximately one hour. They were then sieved on a 1.60 mm screen and the oversized were milled on a Fitzmill grinder equipped with a 790 μm screen and/or on a Forplex grinder.

Layering with Solutions 5 and 6

These two solutions were sprayed on part B. The resulting granulates were dried in the fluidized bed GPCG 1120 for approximately one hour and sieved on a 1.60 μm screen. The oversized were milled on a Fitzmill grinder equipped with a 790 μm screen and/or on a Forplex grinder.

Spraying rate for solutions 1 and 2 was set at about 3.00 kg/min, for solutions 3 and for (sprayed on part A) about 3.25 kg/min and for solutions 5 and 6 (sprayed on part B) also about 3.25 kg/min. Spraying pressure was 3.5 bar.

Drying Step

Parts A and B were dried at 80° C. for about 72 hours.

Milling Step

The dry granulates were milled on a Forplex grinder. One cycle was sufficient to reach the desired particle size (between 150 to 300 μm).

Final Blend

Blend all the milled granulates for 12 minutes at 10 rpm.

Total Composition

| Raw materials | Quantity (kg) | Percentage (%) |
|---|---|---|
| TMC125 | 70 | 20 |
| Lactose EFK | 63 | 18 |
| HPMC 2910 5 cPs | 210 | 60 |
| Montanox 20 DF | 7 | 2 |
| Methylene chloride | 5160 | / |
| Ethyl alcohol 96% | 500 | / |
| Total | 350 | 100 |

The resulting quantity of granulates was about 350 kg, yield about 95%.

2. Results 2.1 Granulometric Distribution

The granulometric distribution of various batches obtained by the above described procedures were in the following ranges:

$D_{10\%}$: 58-94 μm $D_{50\%}$: 229-267 μm $D_{90\%}$: 471-496 μm

Example 2

Preparation of Tablets

| Excipients | Quantity (mg) | Percentage (%) |
|---|---|---|
| TMC125 granulates | 1000.00 | 76.92 |
| Microcristalline cellulose PH302* | 212.90 | 16.38 |
| Reticulated Polyvidone CL USP | 72.80 | 5.60 |
| Silica USP (Aerosil)** | 3.90 | 0.30 |
| Hydrogenated cotton oil** | 10.40 | 0.80 |
| Total | 1300.00 | 100.00 |

*The quantity of Microcristalline Cellulose is adjusted according to the actual assay of TMC125 granulates to have a tablet with a constant weight of 1300 mg.
**An external lubrication of micronised hydrogenated cotton oil + 0.9% Aerosil is performed to solve sticking phenomenon. The quantity sprayed and fixed is not included in the tablet formula (not quantifiable).

Manufacturing of Tablets

Blend

The blend was performed in a 1500 l container with a Soneco blender:
1. Weight and sieve Reticulated Polyvidone CL+Microcristalline Cellulose PH 302+Anhydrous colloidal Silica 200 on a 630 μm screen. Blend then for 12 minutes at 10 rpm.
2. Add TMS 125 granulates and blend for 12 minutes at 10 rpm.
3. Add the hydrogenated cotton oil after sieving on a 630 μm screen and blend for 1 minute at 10 rpm.
4. The blend was sampled according to the analytical protocol but no analytical tests were performed on the blend.

Tableting

For the manufacture of these four tablets batches, the tablet press used was the industrial Fette P1200.

Oblong punches (21.59×10.29 mm) were used.

An external lubrication of micronised hydrogenated cotton oil+0.9% of Aerosil was applied on the punches and the dies to avoid sticking.

The invention claimed is:

1. A pharmaceutical dosage form, comprising at least one particle combined with pharmaceutically acceptable excipients, wherein the particle comprises a co-precipitate applied in a layer surrounding a neutral hydrophilic carrier, and comprises the antiviral compound 4-[[4-amino-5-bromo-6-(4-cyano-2,6-dimethylphenyloxy)-2-pyrimidinyl]amino]benzonitrile, at least one surface-active agent, and at least one hydrophilic polymer, said particle prepared by a process comprising spraying, on a neutral hydrophilic carrier, an organic solution, said solution comprising 4-[[4-amino-5-bromo-6-(4-cyano-2,6-dimethylphenyloxy)-2-pyrimidinyl]amino]benzonitrile, at least one surface active agent, and at least one hydrophilic polymer, wherein the spraying of whole of the solution occurs in at least two separate steps, each of these steps followed by a grinding step of the product obtained at the end of the preceding step, and wherein the particle comprises:

from 15 to 30% in weight of the antiviral compound;
from 30 to 60% in weight of a hydrophilic polymer;
from 15 to 40% in weight of a neutral hydrophilic carrier; and
from 1 to 10% in weight of a surface-active agent;

and wherein the amount of 4-[[4-amino-5-bromo-6-(4-cyano-2,6-dimethylphenyloxy)-2-pyrimidinyl]amino]benzonitrile in the dosage form ranges from 100 mg to 800 mg.

2. A pharmaceutical dosage form according to claim 1 in which the neutral hydrophilic carrier is lactose.

3. A pharmaceutical dosage form according to claim 1 in which the hydrophilic polymer is hydroxypropylmethylcellulose.

4. A pharmaceutical dosage form according to claim 1 in which the non-ionic surfactant is polysorbate.

5. A pharmaceutical dosage form according to claim 1, which is a tablet.

\* \* \* \* \*